(12) United States Patent
Endo et al.

(10) Patent No.: US 11,096,652 B2
(45) Date of Patent: Aug. 24, 2021

(54) BIOACOUSTIC SOUND TESTING DEVICE AND BIOACOUSTIC SOUND TESTING METHOD

(71) Applicant: PANASONIC CORPORATION, Osaka (JP)

(72) Inventors: Mitsuru Endo, Osaka (JP); Maki Yamada, Kanagawa (JP); Noriaki Horii, Kyoto (JP); Chizu Habukawa, Wakayama (JP); Katsumi Murakami, Osaka (JP); Yukio Nagasaka, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 684 days.

(21) Appl. No.: 14/677,272

(22) Filed: Apr. 2, 2015

(65) Prior Publication Data

US 2015/0209000 A1  Jul. 30, 2015

Related U.S. Application Data

(63) Continuation of application No. PCT/JP2014/003884, filed on Jul. 23, 2014.

(30) Foreign Application Priority Data

Jul. 26, 2013  (JP) .............................. JP2013-155811

(51) Int. Cl.
*A61B 7/00* (2006.01)
*A61B 7/04* (2006.01)
(Continued)

(52) U.S. Cl.
CPC .............. *A61B 7/003* (2013.01); *A61B 5/743* (2013.01); *A61B 7/04* (2013.01); *A61B 5/087* (2013.01);
(Continued)

(58) Field of Classification Search
CPC ......... A61B 7/04; A61B 7/003; A61B 5/7257; A61B 2562/0204; A61B 5/08
See application file for complete search history.

(56) References Cited

U.S. PATENT DOCUMENTS 6,443,907 B1    9/2002  Mancy et al.
2003/0018276 A1  1/2003  Mancy et al.
(Continued)

FOREIGN PATENT DOCUMENTS

JP    2004-512066    4/2004
JP    2012-205693    10/2012
(Continued)

OTHER PUBLICATIONS

Extended European Search Report in European Patent Application No. 14829507.4, dated Jul. 6, 2016.
(Continued)

*Primary Examiner* — Rajeev P Siripurapu
*Assistant Examiner* — Michael A Catina
(74) *Attorney, Agent, or Firm* — Greenblum & Bernstein, P.L.C.

(57) ABSTRACT

A bioacoustic sound testing device includes a band power calculator that calculates a band power in a predetermined period for each of a plurality of predetermined frequency bands on the basis of a bioacoustic sound, a reference power calculator that calculates a respiratory airflow reflecting power on the basis of a band power of a band reflecting a respiratory airflow, calculates a specific change reflecting power on the basis of a band power of a band reflecting a specific change in a living body, and calculates a reference power on the basis of the respiratory airflow reflecting power and the specific change reflecting power, and an index value calculator that calculates at least one index value on (Continued)

the basis of the reference power and the band powers of the plurality of predetermined frequency bands.

14 Claims, 14 Drawing Sheets

(51) Int. Cl.
  *A61B 5/00*   (2006.01)
  *A61B 5/087*   (2006.01)
(52) U.S. Cl.
  CPC ........... *A61B 5/7257* (2013.01); *A61B 5/7275* (2013.01); *A61B 5/7278* (2013.01); *A61B 2562/0204* (2013.01)

(56) References Cited

U.S. PATENT DOCUMENTS

| | | | | |
|---|---|---|---|---|
| 2008/0281219 | A1* | 11/2008 | Glickman | A61B 7/003 600/533 |
| 2011/0125044 | A1 | 5/2011 | Rhee et al. | |
| 2011/0288431 | A1 | 11/2011 | Alshaer et al. | |
| 2012/0059280 | A1* | 3/2012 | Horii | A61B 7/003 600/586 |
| 2012/0283598 | A1* | 11/2012 | Horii | A61B 5/087 600/586 |
| 2014/0288452 | A1 | 9/2014 | Mittal | |

FOREIGN PATENT DOCUMENTS

| | | |
|---|---|---|
| JP | 2013-123494 | 6/2013 |
| WO | 2010/044452 | 4/2010 |
| WO | 2011/114669 | 9/2011 |
| WO | 2012/060107 | 5/2012 |
| WO | 2013/061221 | 5/2013 |

OTHER PUBLICATIONS

International Search Report and Written Opinion (ISR/WO) in International Patent Appl. No. PCT/JP2014/003884, dated Nov. 4, 2014, together with an English translation of ISR.

\* cited by examiner

BIOACOUSTIC SOUND TESTING DEVICE AND BIOACOUSTIC SOUND TESTING METHOD

CROSS REFERENCE TO RELATED APPLICATION

This application is a continuation of PCT application No. PCT/JP2014/003884, which was filed on Jul. 23, 2014 based on Japanese Patent Application (No. 2013-155811) filed on Jul. 26, 2013, the contents of which are incorporated herein by reference. Also, all the references cited herein are incorporated as a whole.

BACKGROUND

1. Technical Field

The present disclosure relates to a bioacoustic sound testing device, more particularly, to a bioacoustic sound testing device for supporting the estimation of the state of a living body by measuring bioacoustic sound.

2. Background Art

The treatment of respiratory diseases, such as asthma, often takes a long time. For the treatment of asthma, it is basically necessary to take anti-inflammatory agent for controlling the inflammation of the respiratory tract every day and also take bronchodilator for controlling the stenosis of the respiratory tract at the time of an attack, thereby maintaining the respiratory tract in a properly controlled state for a long time. A medical compound of anti-inflammatory agent and bronchodilator is also used as a daily medicine in some cases.

A comprehensive judgment based on the experience of a medical specialist is required for the judgment of the state of the respiratory tract, and support using objective indexes obtained from testing devices is extensively desired to make a comprehensive and appropriate judgment. As a testing device of this kind, for example, the bioacoustic sound testing device described in WO2012/060107 is available.

SUMMARY OF THE INVENTION

However, in WO2012/060107, further improvements are required.

In one general aspect, the techniques are disclosed here that a bioacoustic sound testing device comprising:

a band power calculator that calculates a band power in a predetermined period for each of a plurality of predetermined frequency bands on the basis of a bioacoustic sound;

a reference power calculator that calculates a respiratory airflow reflecting power on the basis of a band power of a band reflecting a respiratory airflow and at least partially including any of frequencies ranging from 250 Hz or more to 1050 Hz or less, calculates a specific change reflecting power on the basis of a band power of a band reflecting a specific change in a living body and at least partially including any of frequencies ranging from 1250 Hz or more to 1550 Hz or less, and calculates a reference power on the basis of the respiratory airflow reflecting power and specific change reflecting power; and an index value calculator that calculates at least one index value on the basis of the reference power and the band powers of the plurality of predetermined frequency bands.

These general and specific aspects may be implemented using a system, a method, and a computer program, and any combination of systems, methods, and computer programs.

With the present disclosure, an index value properly reflecting the state of the respiratory tract can be obtained while the number of the sensors for measuring the bioacoustic sound is reduced. Furthermore, since the number of the sensors can be reduced, the operation of the apparatus is simplified.

Figure 1:
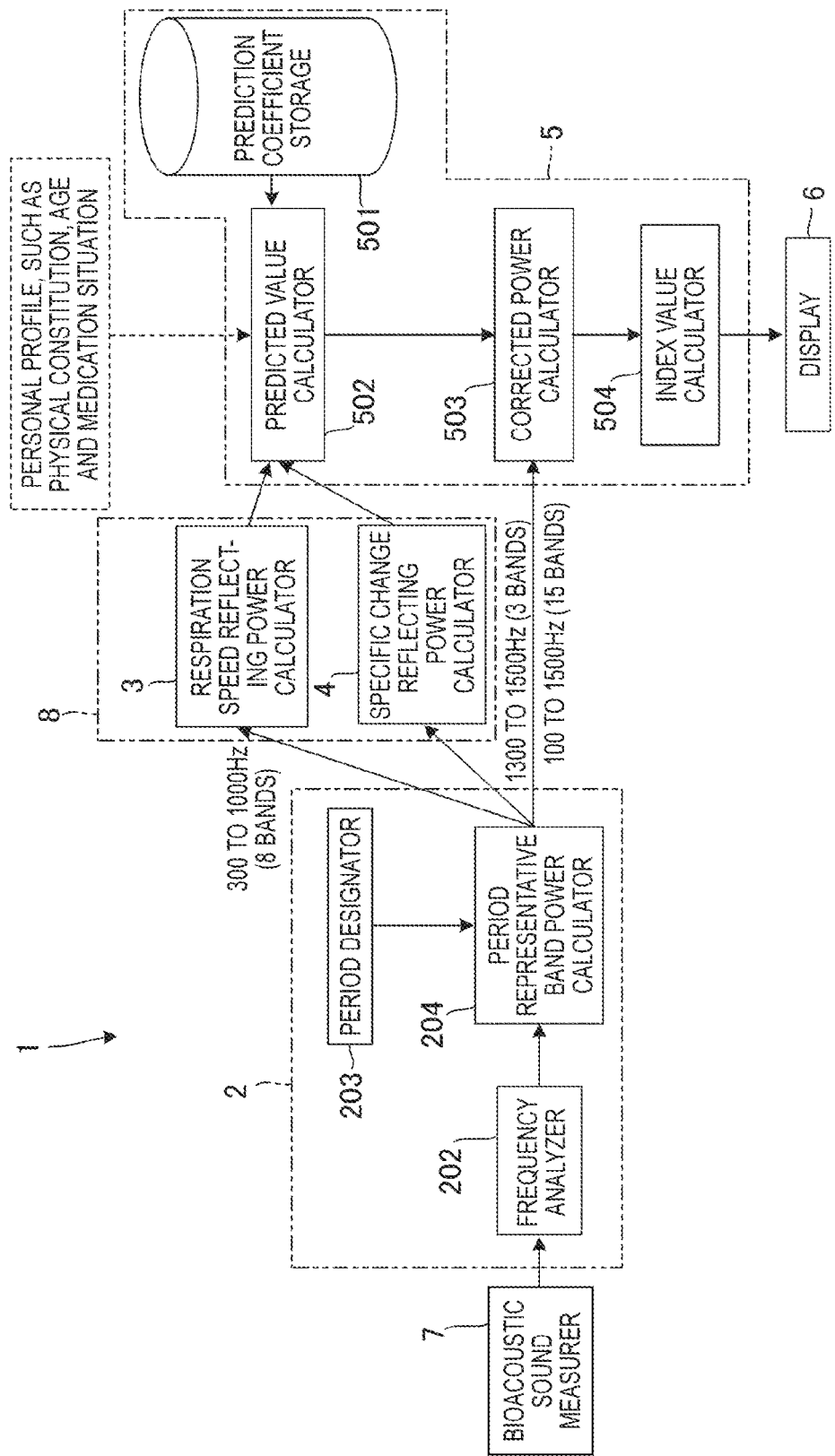
FIG. 1 is a block diagram illustrating an outline configuration of a bioacoustic sound testing device according to an embodiment of the present disclosure.

DETAILED DESCRIPTION OF THE EXEMPLARY EMBODIMENTS (Knowledge Becoming the Basis for the Present Disclosure)

The inventors found that the techniques described in WO2012/060107 cause following problems.

It is known that respiratory sound becomes stronger as respiratory airflow is higher and becomes weaker as physical constitution is larger, and the index value of the standard of the respiratory sound in which the influence of these is reduced is known. In the bioacoustic sound testing device described in WO2012/060107, respiratory sound is measured at two points on the cervical region and the chest, and the ratio of the powers at the cervical region and the chest is used to reduce the influence of the respiratory airflow and the physical constitution. Furthermore, one of a plurality of index values is obtained by predicting the state in a high band from that in the band reflecting respiratory airflow at the cervical region, and a predictive residue is calculated, whereby the influence of the respiratory airflow is reduced.

However, the bioacoustic sound testing device described in WO2012/060107 described above has a problem in that the operation thereof becomes complicated because two sensors are used for the cervical region and the chest. In the comparison between the cervical region and the chest, the testing at the chest close to the peripheral respiratory tract is more suited for the detection of the small change in the state of the respiratory tract, whereby it is assumed that the state of the respiratory tract can be estimated by using only the sensor for the chest; however, since the respiration sound at the chest is weaker, the influence due to factors other than the state of the respiratory tract that is desired to be known is significant, whereby an index value properly reflecting the state of the respiratory tract is not obtained. Hence, the two sensors for the chest and the cervical region are required to obtain the index value properly reflecting the state of the respiratory tract.

Therefore, the inventors considered following improvements.

(1) In a first aspect of the present disclosure, there is provided a bioacoustic sound testing device according to the present disclosure includes a band power calculator that calculates a band power in a predetermined period for each of a plurality of predetermined frequency bands on the basis of a bioacoustic sound; a reference power calculator that calculates a reference power on the basis of the band power of the band at least partially including any of frequencies ranging from 250 Hz or more to 1050 Hz or less and the band power of the band at least partially including any of frequencies ranging from 1250 Hz or more to 1550 Hz or less among from the band powers of the plurality of predetermined frequency bands; and an index value calculator that calculates at least one index value on the basis of the reference power and the band powers of the plurality of predetermined frequency bands.

With the above-mentioned configuration, an index value properly reflecting a state of a respiratory tract is obtained.

(2) In the above aspect, exemplarily, the index value calculator includes: a predicted value calculator that calculates a predicted value for each of the bands on the basis of at least the reference power; and a corrected power calculator that calculates a corrected power for each of the bands by subtracting the predicted value for each of the bands from the band power for each of the bands. The index value calculator calculates an index value on the basis of the corrected power.

(3) In the above aspect, exemplarily, the bands where correction is performed include 700 Hz and 1400 Hz.

(4) In the above aspect, exemplarily, the index value calculator performs correction for one band on the basis of each of two or more kinds of reference powers and sets each corrected power as the index value.

(5) In the above aspect, exemplarily, the two or more kinds of reference powers include a reference power based on weighted addition of respiratory airflow reflecting power and specific change reflecting power and a reference power based on weighted subtraction between the respiratory airflow reflecting power and the specific change reflecting power.

(6) In the above aspect, exemplarily, the device further includes a display that displays the index value.

(7) In the above aspect, exemplarily, the display plots two or more kinds of index values along a time axis.

(8) In the above aspect, exemplarily, the display displays two kinds of index values as a two-dimensional map and displays the two kinds of index values along time series by connecting measurement points.

(9) In the above aspect, exemplarily, the index value calculator calculates the index value on the basis of a linear sum of two or more corrected powers.

(10) In the above aspect, exemplarily, the predicted value calculator predicts a standard value of the band power corresponding to the reference power on the basis of a measurement sample in a standard state.

(11) In the above aspect, exemplarily, the band power calculator includes: a frequency analyzer that performs frequency analysis for a measured bioacoustic sound; a period designator that designates a period to be analyzed among from a plurality of respiration periods; and a period representative band power calculator that calculates a representative band power in the period designated by the period designator for the plurality of predetermined frequency bands on the basis of the bioacoustic sound subjected to frequency analysis using the frequency analyzer.

(12) In the above aspect, exemplarily, a bioacoustic sound measurer for measuring the bioacoustic sound measures the bioacoustic sound at one point on a chest of a living body.

(12) In the above aspect, exemplarily, the band reflecting the specific change is a band in which a difference between a power after a medication of bronchodilator and a power after the medication of anti-inflammatory agent is large.

(13) In the above aspect, exemplarily, the reference power is an average value of the powers of continuous wide bands including the band reflecting the respiratory airflow and the band reflecting the specific change.

(14) In the above aspect, exemplarily, the reference power is an average value of the powers of the bands including frequencies ranging from 150 Hz or more to 1550 Hz or less.

A preferred embodiment according to the present disclosure will be described below in detail referring to the drawings.

FIG. 1 is a block diagram illustrating an outline configuration of a bioacoustic sound testing device according to an embodiment of the present disclosure. In the figure, a bioacoustic sound testing device 1 according to this embodiment includes a bioacoustic sound measurer 7, a band power calculator 2, a reference power calculator 8, an index value calculator 5, and a display 6. The reference power calculator 8 includes a respiratory airflow reflecting power calculator 3 and a specific change reflecting power calculator 4. The bioacoustic sound measurer 7 is a measuring instrument with a sensor, such as an electronic stethoscope, and is used to measure bioacoustic sound at one point on the chest of a living body. Although the bioacoustic sound is acquired in real time in this embodiment, a recording function may be provided so that recorded bioacoustic sound is acquired. Furthermore, a sticking type or built-in type sensor may also be used. The band power calculator 2 is used to calculate the band power in a predetermined period for a predetermined plurality of frequency bands on the basis of bioacoustic sound, and includes a frequency analyzer 202 for performing frequency analysis for the bioacoustic sound measured using the bioacoustic sound measurer 7; a period designator 203 for designating a period to be analyzed from among a plurality of respiration periods; and a period representative band power calculator 204 for calculating the representative band power in the period designated by the period designator 203 for the predetermined plurality of frequency bands on the basis of the bioacoustic sound that has been_subjected to frequency analysis using the frequency analyzer 202.

The frequency analyzer 202 performs frequency analysis using, for example, fast Fourier transform. The period designator 203 designates a period to be used for the analysis performed using the period representative band power calculator 204 described later. The period to be designated may merely be designated under the conditions that inhalation is performed, that the level of the sound is appropriate and that noise is low and so on, and the professional knowledge of a medical doctor is not required. Extraction of the period can be made automatically by executing a program so that the above-mentioned conditions are satisfied. Furthermore, the respiration period may be designated manually through GUI (Graphical User Interface) or the like.

The period representative band power calculator 204 calculates the power representing the period designated by the period designator 203, for example, for each of 15 bands (bands having central frequencies of 100 Hz, 200 Hz, 300 Hz, . . . , 1300 Hz, 1400 Hz and 1500 Hz and having a bandwidth of 100 Hz). For example, powers in analysis frame unit for frequency analysis are averaged throughout analysis frames included in the period. In this case, since the width of each band is 100 Hz, the band having a central frequency of 100 Hz ranges from 50 to 150 Hz, the band having a central frequency of 200 Hz ranges from 150 to 250 Hz, the band having a central frequency of 300 Hz ranges from 250 to 350 Hz, . . . . , the band having a central frequency of 1300 Hz ranges from 1250 to 1350 Hz, the band having a central frequency of 1400 Hz ranges from 1350 to 1450 Hz, and the band having a central frequency of 1500 Hz ranges from 1450 to 1550 Hz. The "15" frequency bands are just taken as examples and the number of the frequency bands may be larger or smaller than 15. Moreover, the bandwidth is not limited to 100 Hz but may be variable for each band. Also, in a similar way, the period representative band power calculator 204 calculates the period representative band powers of eight bands having central frequencies of 300 Hz, 400 Hz, 500 Hz, 600 Hz, 700 Hz, 800 Hz, 900 Hz and 1000 Hz. These eight bands are bands reflecting the speed of respiration. The "eight" frequency bands are just taken as examples and the number of the frequency bands may be larger or smaller than eight.

Still further, in a similar way, the period representative band power calculator 204 calculates the period representative band powers of three bands having central frequencies of 1300 Hz, 1400 Hz and 1500 Hz. These three bands are bands reflecting a specific change in the living body. More specifically, the difference between the power after the medication of bronchodilator and the power after the medication of anti-inflammatory agent is large in the bands. The "three" frequency bands reflecting the specific change in the living body are just taken as examples and the number of the frequency bands may be larger or smaller than three.

After calculating the band powers of the 15 bands at the central frequencies of 100 to 1500 Hz, the period representative band power calculator 204 outputs the calculated band powers of the 15 bands to the corrected power calculator 503 of the index value calculator 5. Furthermore, after calculating the band powers of the eight bands at the central frequencies of 300 to 1000 Hz, the period representative band power calculator 204 outputs the calculated band powers of the eight bands to the respiratory airflow reflecting power calculator 3 included in the reference power calculator 8. Moreover, after calculating the band powers of the three bands at the central frequencies of 1300 to 1500 Hz, the period representative band power calculator 204 outputs the calculated band powers of the three bands to the specific change reflecting power calculator 4 included in the reference power calculator 8.

The respiratory airflow reflecting power calculator 3 calculates respiratory airflow reflecting power by averaging the band powers of the eight bands serving as bands reflecting the respiratory airflow. In this embodiment, although the bands reflecting the respiratory airflow in the respiratory airflow reflecting power calculator 3 have frequencies ranging from 250 Hz or more to 1050 Hz or less (from a central frequency of 300 to 1000 Hz), the bands may at least partially include any of frequencies ranging from 250 or more to 1050 Hz or less. The specific change reflecting power calculator 4 calculates specific change reflecting power by averaging the band powers of the three bands serving as bands reflecting the specific change other than the respiratory airflow. In this embodiment, although the bands reflecting the specific change in the specific change reflecting power calculator 4 have frequencies ranging from 1250 or more to 1550 Hz or less (from a central frequency of 1300 to 1500 Hz), the bands may at least partially include any of frequencies ranging from 1250 or more to 1550 Hz or less. Furthermore, operation other than averaging may also be used as the operation for calculating the respiratory airflow reflecting power and the specific change reflecting power.

The index value calculator 5 is used to calculate at least one index value from the respiratory airflow reflecting power calculated by the respiratory airflow reflecting power calculator 3, the specific change reflecting power calculated by the specific change reflecting power calculator 4 and the band power calculated by the band power calculator 2, and includes a prediction coefficient storage 501 for holding a prediction coefficient for each band to predict a predicted value for each band; a predicted value calculator 502 for calculating a predicted value for each band on the basis of the respiratory airflow reflecting power, the specific change reflecting power and the prediction coefficient for each band; the corrected power calculator 503 for calculating corrected power for each band by subtracting the predicted value for each band from the representative band power for each band; and an index value calculator 504 for calculating the index value on the basis of the corrected power for each band. Personal profile (for example, physical constitution, age, and medication situation) may be input to the predicted value calculator 502. Although respiratory sound is generally influenced by the level of the power of each band depending on the respiratory airflow, the degree of the influence differs for each band, and the influence of factors other than the respiratory airflow also differs for each band. In this embodiment, the power in a band susceptible to the influence of the respiratory airflow or the like is set to reference power and a standard power value corresponding to the reference power is predicted so that the desired information on the state of the respiratory tract remains in the difference (predictive residue) between the predicted value and the measured value and so that the influence of the other factors is eliminated. The reference power may merely be calculated on the basis of the respiratory airflow reflecting power calculated by the respiratory airflow reflecting power calculator 3 and the specific change reflecting power calculated by the specific change reflecting power calculator 4. In other words, the reference power is calculated by the reference power calculator 8.

The display 6 has a displaying means, such as a liquid crystal display device or an organic EL display device, and displays the index values in a visible mode. In the case that the index values are displayed together with the samples of the past index values stored, the comparison among the index values can be performed. For example, the display plots two or more index values along a time axis. Furthermore, the display displays two index values as a two-dimensional map and displays the index values along time series by connecting measurement points.

Next, the operation of the bioacoustic sound testing device 1 according to this embodiment will be described.

Figure 2:
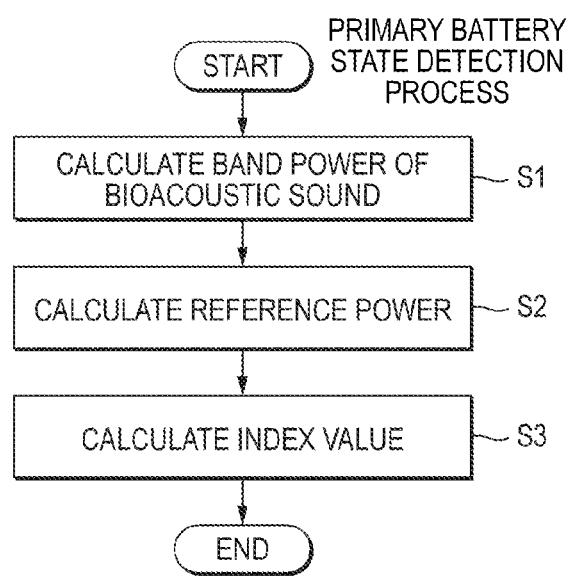
FIG. 2 is a flow chart illustrating the operation of the bioacoustic sound testing device shown in FIG. 1.

FIG. 2 is a flow chart illustrating the operation of the bioacoustic sound testing device 1 according to this embodiment. In the figure, the band power calculator 2 first calculates the band power in a predetermined period for the predetermined plurality of frequency bands on the basis of bioacoustic sound (at step S1). In other words, the band power calculator 2 sequentially executes the step of measuring the bioacoustic sound at one point on the chest of the living body (bioacoustic sound measurement step), the step of performing frequency analysis for the measured bioacoustic sound (frequency analysis step), the step of manually designating the period to be analyzed from among the plurality of respiration periods through GUI or the like or automatically designating the period on the basis of a predetermined program (period designation step), the step of calculating the representative band power in the designated period for the predetermined plurality of frequency bands on the basis of the bioacoustic sound that has been_subjected to frequency analysis (period representative band power calculation step). In this case, the frequency bands are 15 bands (hereafter simply referred to as "15 bands") having central frequencies of 100, 200, . . . , 1500 Hz and having a bandwidth of 100 Hz. The stethoscopic diagnosis position on the chest includes not only a position on the front face of the living body but also a position on the rear face or a side face thereof.

After calculating the band power of the bioacoustic sound, the band power calculator 2 outputs the band powers of the bands having central frequencies of 300 to 1000 Hz and strongly reflecting the respiratory airflow among the 15 bands and the band powers of the bands having central frequencies of 1300 to 1500 Hz and strongly reflecting the specific change in the living body (for example, the change due to respiratory tract stenosis or the differences between respiratory tract inflammation and respiratory tract stenosis) to the reference power calculator 8. On the basis of these band powers, the reference power calculator 8 calculates the reference power (at step S2). In other words, the reference power calculator 8 executes a reference power calculation step. The calculated reference power is then output to the index value calculator 5.

More specifically, the respiratory airflow reflecting power calculator 3 calculates the respiratory airflow reflecting power on the basis of the band powers of the bands having central frequencies of 300 to 1000 Hz. In other words, the respiratory airflow reflecting power calculator 3 calculates the respiratory airflow reflecting power by averaging the respiratory airflow values of the bands reflecting the respiratory airflow among the 15 bands. The calculated respiratory airflow reflecting power is then output to the index value calculator 5.

Furthermore, the specific change reflecting power calculator 4 calculates the specific change reflecting power on the basis of the band powers of the bands having central frequencies of 1300 to 1500 Hz. In other words, the specific change reflecting power calculator 4 calculates the specific change reflecting power by averaging the specific change values of the bands reflecting the specific change among the 15 bands. The calculated specific change reflecting power is then output to the index value calculator 5.

On the basis of the reference power (the respiratory airflow reflecting power and the specific change reflecting power) calculated by the reference power calculator 8 and the band power calculated by the band power calculator 2, the index value calculator 5 calculates one or more index values (at step S3). In other words, the index value calculator 5 sequentially executes the step of reading the prediction coefficient for each band to predict the predicted value for each band (prediction coefficient reading step); the step of calculating the predicted value for each band on the basis of the respiratory airflow reflecting power, the specific change reflecting power and the prediction coefficient for each band (predicted value calculation step); the step of calculating the corrected power for each band by subtracting the predicted value for each band from the representative band power for each band (corrected power value calculation step); and the step of calculating at least one index value on the basis of the corrected power for each band (index value calculation step). The index value calculated by the index value calculator 5 is obtained as a single corrected power value or as the linear sum of a plurality of corrected powers.

It may be possible that a plurality of inhalation periods are designated at step S1 and that a representative value (for example, a median value) is determined from among the index values for the designated periods at step S3.

Next, the features of the bioacoustic sound testing device 1 according to this embodiment will be described in detail.

Figure 3:
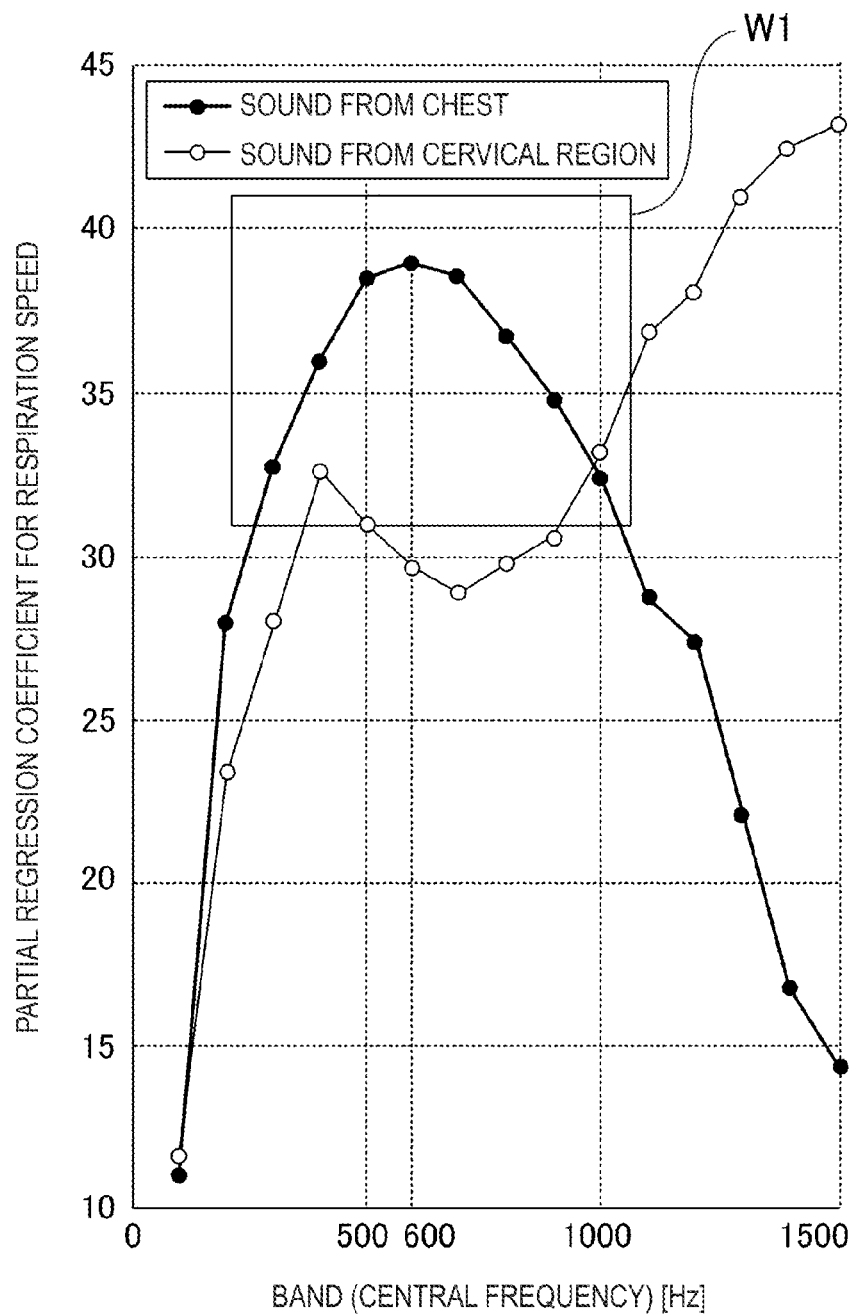
FIG. 3 is a view illustrating the examples of the bands reflecting respiratory airflow in the bioacoustic sound testing device shown in FIG. 1.

FIG. 3 is a view illustrating the examples of the bands reflecting the respiratory airflow. In the figure, the horizontal axis represents the band (central frequency) and the vertical axis represents the partial regression coefficient for respiratory airflow. The measurement of bioacoustic sound was performed on both the cervical region and the chest, and at the same time, respiratory airflow was measured using a respiration flow meter. In particular, the sound from the chest was measured at the second intercostal space on the median line of the right clavicle. Multiple regression analysis for the power at the measurement position and for each band depending on the respiratory airflow and the height was performed using the data of 61 people, and partial regression coefficients for the respiratory airflow were obtained. As shown in the figure, it was found that, although the respiratory airflow dependency of the power at the cervical region is high up to the high-frequency range, the respiratory airflow dependency of the power at the chest is low in the low and high frequency ranges with 600 Hz at the center. The band W1 reflecting the respiratory airflow in the power at the chest is, for example, in the range from 300 to 1000 Hz.

Figure 4:
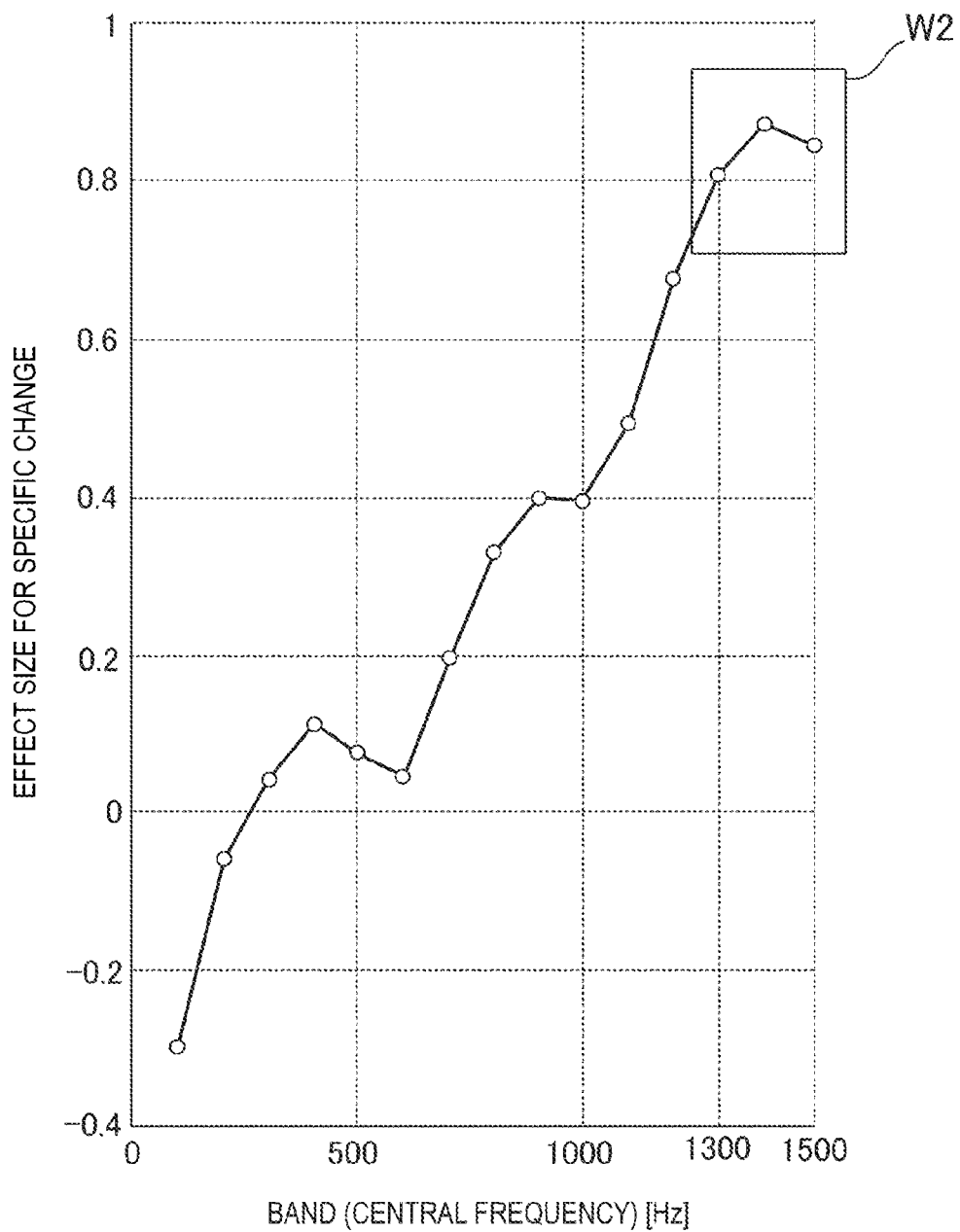
FIG. 4 is a view illustrating examples of the bands reflecting a specific change in the bioacoustic sound testing device shown in FIG. 1.

FIG. 4 is a view illustrating examples of the bands reflecting a specific change in the state of the respiratory tract. In the figure, the horizontal axis represents the band (central frequency) and the vertical axis represents the effect size for the specific change. This figure shows the effect size obtained for each band in the case that the respiratory sound after the medication in a group (20 people) having been improved by daily controller medication is compared with the respiratory sound after the medication in a group (19 people) whose respiratory tracts were dilated using only bronchodilator medication. As shown in the figure, it is found that the effect size is relatively large in a band W2 ranging from 1300 to 1500 Hz. In this band W2, the power of the respiratory sound improved by daily controller medication tends to be higher than those in the other bands in comparison with the state before the medication; and depending on the type of bronchodilator, the power tends to be lower than those in the other bands in comparison with that the state before the medication; the trend becomes opposite.

In the case that the power of the band in which the difference between the respiratory sound improved by daily controller medication and the respiratory sound obtained after the respiratory tract was dilated by only bronchodilator medication is large is set to the specific change reflecting power and that the power obtained by linear operation in the direction of adding the respiratory airflow reflecting power to the specific change reflecting power is set to the reference power, the index value emphasizing the change in the respiratory sound due to the improvement in chronic inflammation can be calculated. Conversely, in the case that the power obtained by linear operation in the direction of subtracting the specific change reflecting power from the respiratory airflow reflecting power is set to the reflecting power, the index value emphasizing the change in the respiratory sound due to the improvement in respiratory tract stenosis can be calculated.

Figure 5:
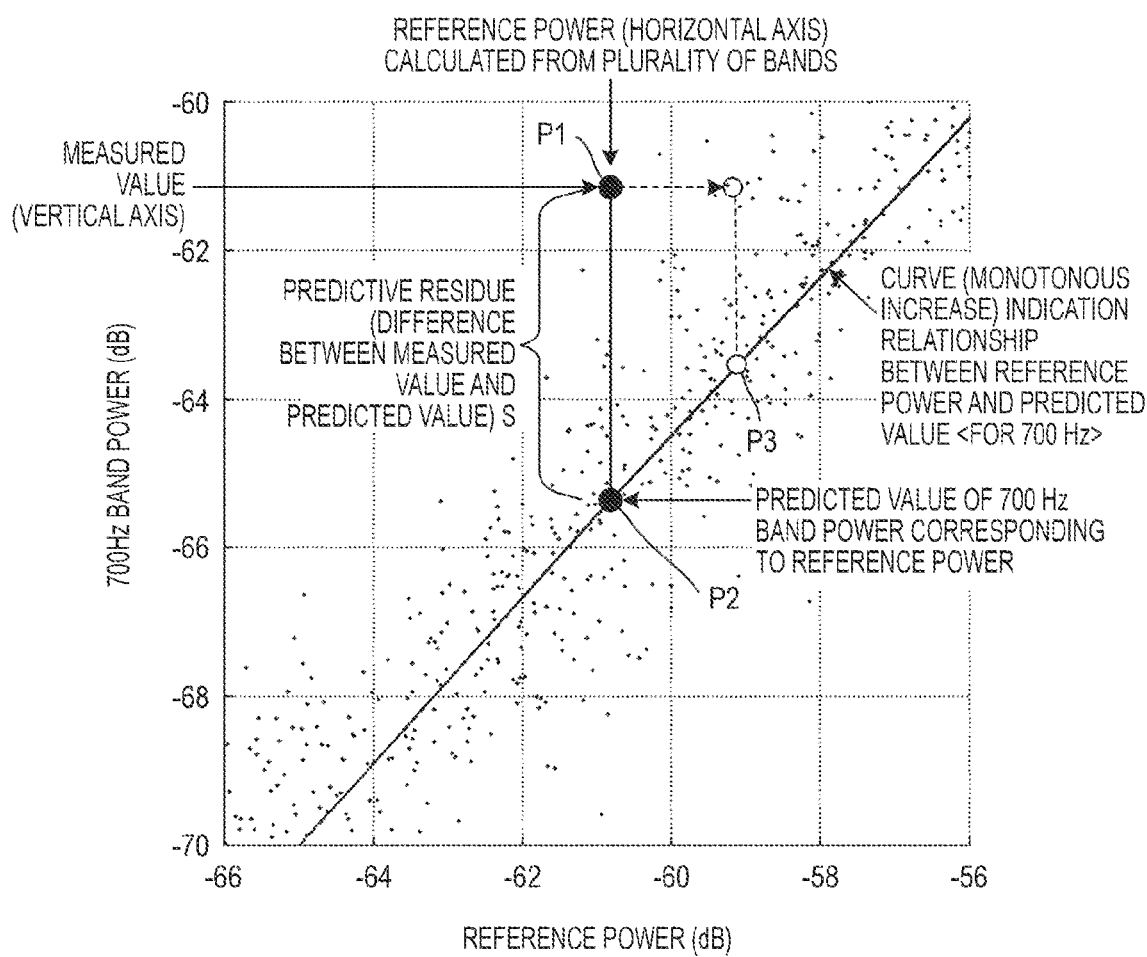
FIG. 5 is a view illustrating an example indicating the state of correction in the bioacoustic sound testing device shown in FIG. 1.

FIG. 5 is a view illustrating an example indicating the state of correction. In this embodiment, the correction is performed for the 15 bands on the basis of the reference power, and the index value is obtained from the corrected power for each band. The reference power is commonly used for the 15 bands. The 15 bands in which the correction is performed include 700 Hz and 1400 Hz. FIG. 5 exemplifies the correction of the power particularly at the central frequency of 700 Hz.

A method for obtaining the prediction coefficient will herein be described. Prior to the use of the bioacoustic sound testing device according to this embodiment, it is assumed that numerous respiratory sound samples of medical cases not diagnosed with asthma by medical doctors or medical cases diagnosed with asthma but being good in the state of the respiratory tract have been collected and adopted as the standard respiratory sound. The standard value (the value of the band power value in the standard state) can be obtained by analyzing the relationship between the power at the single band of 700 Hz and the reference power based on the plurality of bands. Various methods, such as regression analysis, are available as analysis methods, and a parameter representing physical constitution, such as height, and a parameter representing age may be used additionally in addition to the reference power. Furthermore, it may also be possible that the reference power is divided into a plurality of zones depending on the level thereof, that representative values based on the least-squares method are determined for the respective zones, and that the representative values are connected. These numerical values representing the relationship between the reference power and the standard value of the band power, such as the coefficients by regression analysis and the representative values for the respective zones, are referred to as prediction coefficients.

Since the power of a single band usually becomes larger as the reference power becomes larger, a monotonous increase relationship is obtained. Although the relationship is generally linear, the relationship is non-linear if it is observed minutely. First, an example in the case that the respiratory airflow reflecting power is set to the reference power is shown. Referring to FIG. 5, the horizontal axis represents the reference power (dB) and the horizontal axis represents the value (dB) of the band power at 700 Hz. Furthermore, each "dot" in the figure indicates a measurement sample. Moreover, two "black circles" indicate measured value P1 and predicted value P2 to which attention is paid for explanation. The predicted value P2 is the standard value predicted from the reference power. The predictive residue S obtained by calculating the difference between the measured value P1 and the predicted value P2 is the corrected power. Since the residual is obtained from the predicted value that is assumed to be attained in the standard state of the respiratory tract, the difference from the standard state is represented by a numerical value. In this example, the reference power of correction (a) is used. The correction (a) is used to reduce the influence due to respiratory airflow. It has been confirmed from data that the predictive residue obtained by using the reference power of this correction hardly has respiratory airflow dependency, physical constitution dependency and age dependency.

The reference power of the correction (a): base_pow=Fpow where base_pow represents the reference power and Fpow represents the respiratory airflow reflecting power.

Next, a case in which two kinds of reference powers are used will be described as an example. Two or more kinds of reference powers can be used for the correction. When a case ("white circle P3") is considered in which the expression of the reference power is modified and the reference power has increased, as the reference power increases, the predicted value also increases, but the power of a single band remains unchanged, whereby the predictive residue S decreases. Conversely, the predictive residue S increases when the reference power decreases. Expressions in which the specific change reflecting power is added or subtracted to increase or decrease the reference power are the expressions of the reference power of the correction (b) and the reference power of the correction (c). However, it is necessary to prepare a predicted value corresponding to the expression of the reference power after the modification. The correction (b) is used to reduce the influence of respiratory airflow and the influence of respiratory tract stenosis, and the correction (c) is used to reduce the influence of respiratory airflow and to emphasize the influence of respiratory tract stenosis.

The reference power of the correction (b): base_pow=Fpow+0.3×Npow

The reference power of the correction (c): base_pow=Fpow−0.2×Npow where base_pow represents the reference power, Fpow represents the respiratory airflow reflecting power, and Npow represents the specific change reflecting power.

The band in which the specific change reflecting power is decreased by the effect of bronchodilator (the improvement of respiratory tract stenosis) is the band in which the specific change reflecting power is increased by the effect of anti-inflammatory agent (the improvement of respiratory tract inflammation); hence, in the correction (b) in which the weighted addition of the specific change reflecting power to the respiratory airflow reflecting power is performed, the power after the correction tends to increase due to the improvement of respiratory tract stenosis and the power after the correction tends to decrease due to the improvement of respiratory tract inflammation. Furthermore, in the correction (c) in which the weighted subtraction of the specific change reflecting power from the respiratory airflow reflecting power is performed, the power after the correction tends to decrease due to the improvement of respiratory tract stenosis and the power after the correction tends to increase due to the improvement of respiratory tract inflammation.

The weights of the calculation expressions of the correction (b) and the correction (c) were adjusted to the extent that the change due to β2 stimulant becomes 0 in average in the correction (b) and to the extent that the change due to anti-inflammatory agent becomes 0 in average in the correction (c). The weights of the correction (b) and the correction (c) were set, for example, to "0.3" for the correction (b) and to "0.2" for the correction (c). Hence, it is assumed that the index value (b) obtained by the correction (b) mainly represents the degree of respiratory tract inflammation and that the index value (c) obtained by the correction (c) mainly represents the degree of respiratory tract stenosis.

As described above, the correction can be performed by preparing a plurality of reference power calculation expressions and by obtaining standard values corresponding thereto. In addition, standard values are also obtained similarly beforehand for each single band other than 700 Hz and correction is performed. Also in the correction (b), the degree of respiratory tract stenosis is expressed in a band in which the power increases due to the deterioration of respiratory tract stenosis, for example, the 1400 Hz band. In other words, the standard values exist in the number of individual bands for each definition of the reference power. However, for bands that are not used in the end, operation is not required to be performed and parameters are not required to be stored.

As a modification of the correction (b), the average value of the powers of wide bands (for example, 300 to 1500 Hz and 200 to 1500 Hz) including the respiratory airflow reflecting power band and the specific change reflecting power band may be set as the reference power. In addition, in the case that noise tends to be included in a band, the band may be eliminated or interpolation may be performed by using the powers of the adjacent bands.

Furthermore, the effects obtained by the correction (c) and the correction (b) are also obtained respectively when the power value at 700 Hz after the correction and the power value at 1400 Hz after the correction are subjected to weighted addition or weighted subtraction.

The index value can be used properly depending on the contents of medication.

Furthermore, the "15" frequency bands are just taken as examples and the frequency bands may be defined otherwise.

When the correction is performed similarly at 1400 Hz as in the example at 700 Hz shown in FIG. 5, the correction is performed for the two bands (700 Hz and 1400 Hz) on the basis of the common reference power (correction (a)) and the respective corrected powers are used as index values; however, the correction may also be performed for one band (for example, 700 Hz) on the basis of each of two or more kinds of reference powers (for example, the reference powers of the correction (b) and the correction (c)) and the respective corrected powers may be used as index values. In this case, the two or more kinds of reference powers include the reference power that is based on the weighted addition of the respiratory airflow reflecting power and the specific change reflecting power and also include the reference power that is based on the weighted subtraction between the respiratory airflow reflecting power and the specific change reflecting power.

Figure 6:
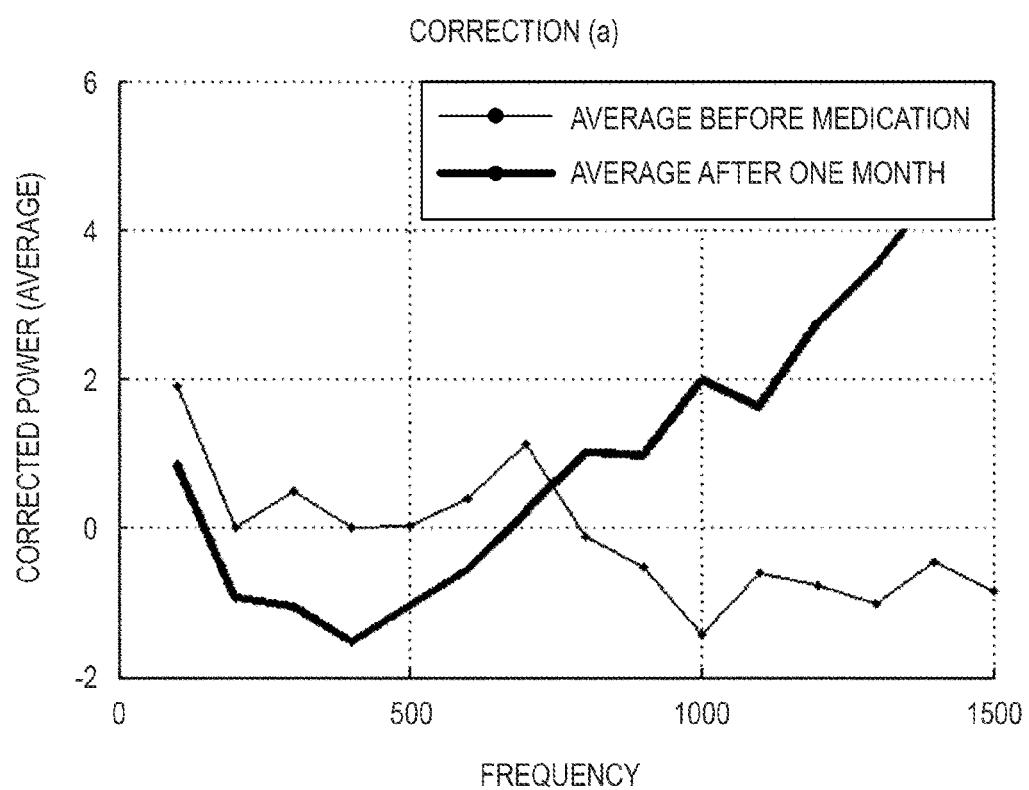
FIG. 6 is a graph illustrating the frequency dependency of power after the correction by correction (a)
Figure 7:
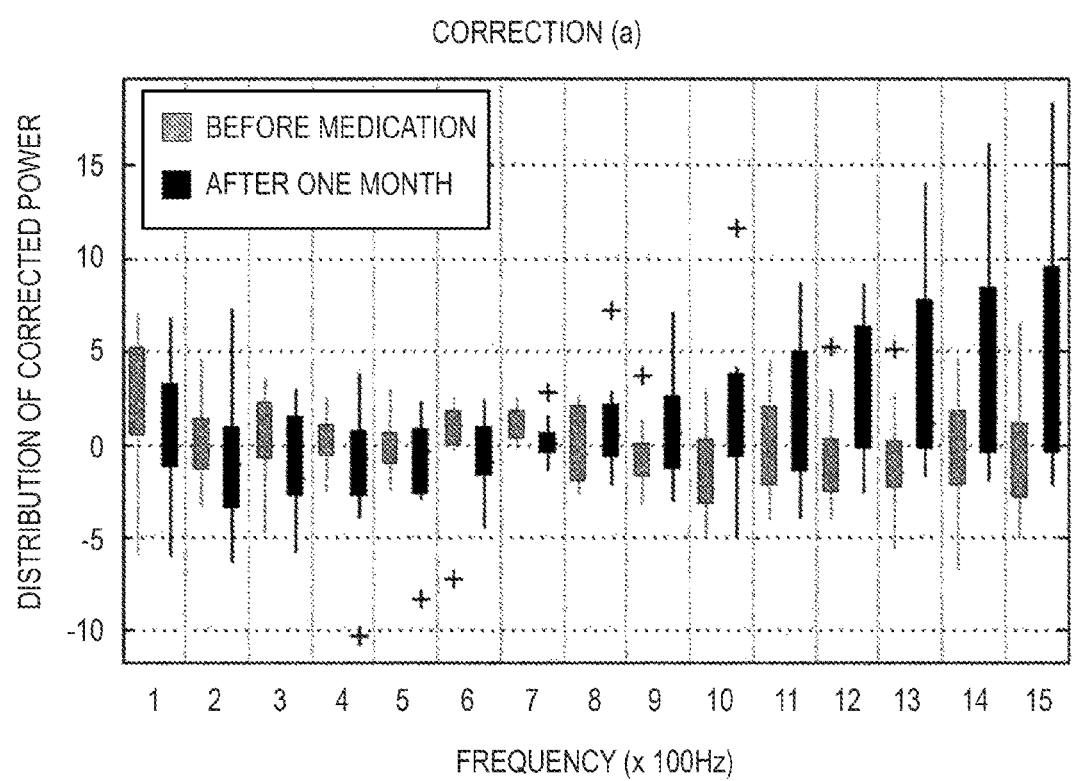
FIG. 7 is a box plot illustrating the frequency dependency of power distribution after the correction by correction (a)
Figure 8:
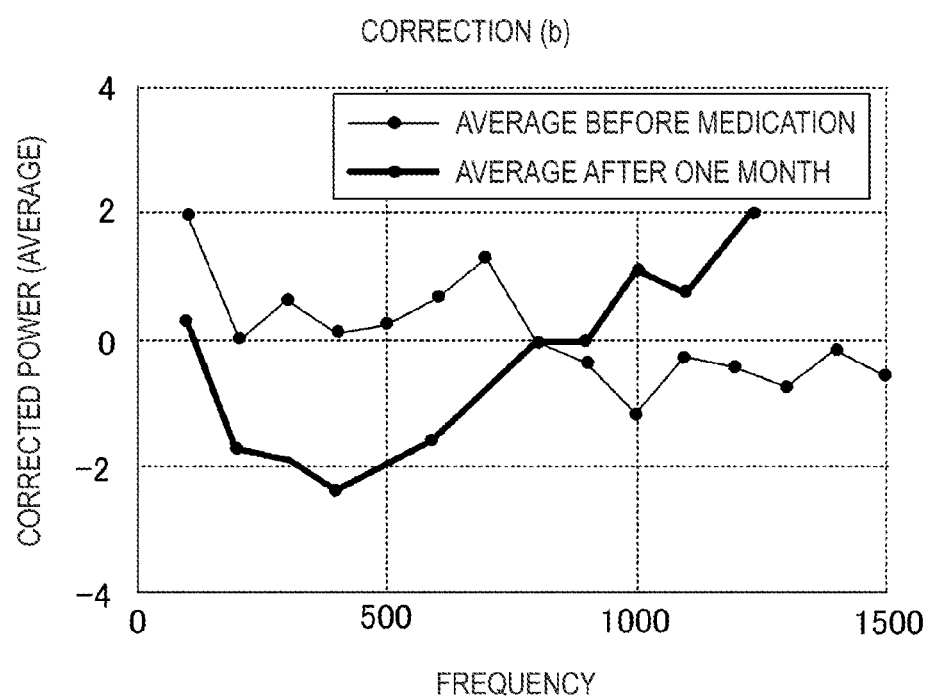
FIG. 8 is a graph illustrating the frequency dependency of power after the correction by correction (b)
Figure 9:
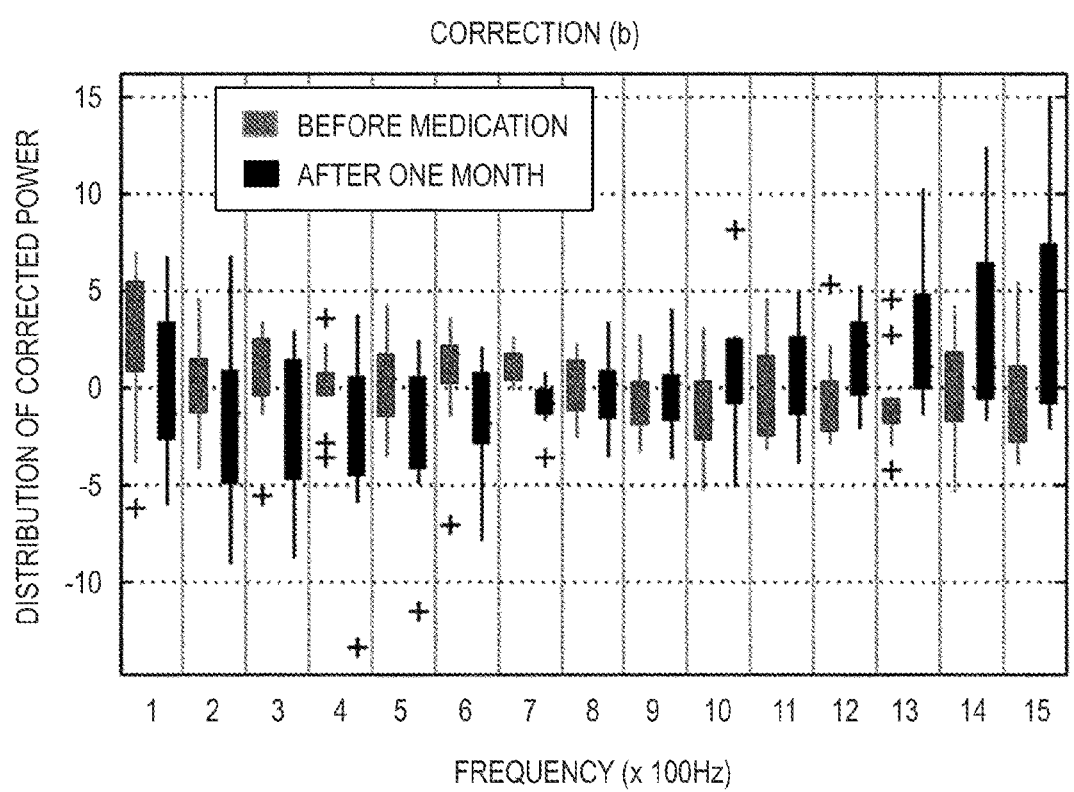
FIG. 9 is a box plot illustrating the frequency dependency of power distribution after the correction by the correction (b)

FIG. 6 is a graph illustrating the frequency dependency of the power (average value) after the correction by the correction (a). Furthermore, FIG. 7 is a box plot illustrating the frequency dependency of power distribution after the correction by the correction (a). In addition, FIG. 8 is a graph illustrating the frequency dependency of the power (average value) after the correction by the correction (b). Furthermore, FIG. 9 is a box plot illustrating the frequency dependency of the power distribution after the correction by the correction (b). The figures respectively indicate the statistics of "11" medical cases at the start time of the medication of long-term controller and after one month from the start of the medication. When the average values before and after the medication are compared referring to FIGS. 6 and 8, the powers are decreased in the low and middle bands before and after the medication; however, there is no significant difference in the amount of the change in any of the bands from 300 to 700 Hz. When FIG. 6 and FIG. 8 are compared, the difference in the correction (b) is larger than that in the correction (a) at up to 700 Hz. On the other hand, referring to FIGS. 7 and 9, variation is small particularly at 700 Hz and there is little overlapping of distribution before and after the medication; hence, it is found that attention should be paid particularly to the value at 700 Hz as the index value. When FIG. 7 and FIG. 9 are compared, the overlapping of distribution of corrected powers in the correction (b) is less than that in the correction (a).

Figure 10:
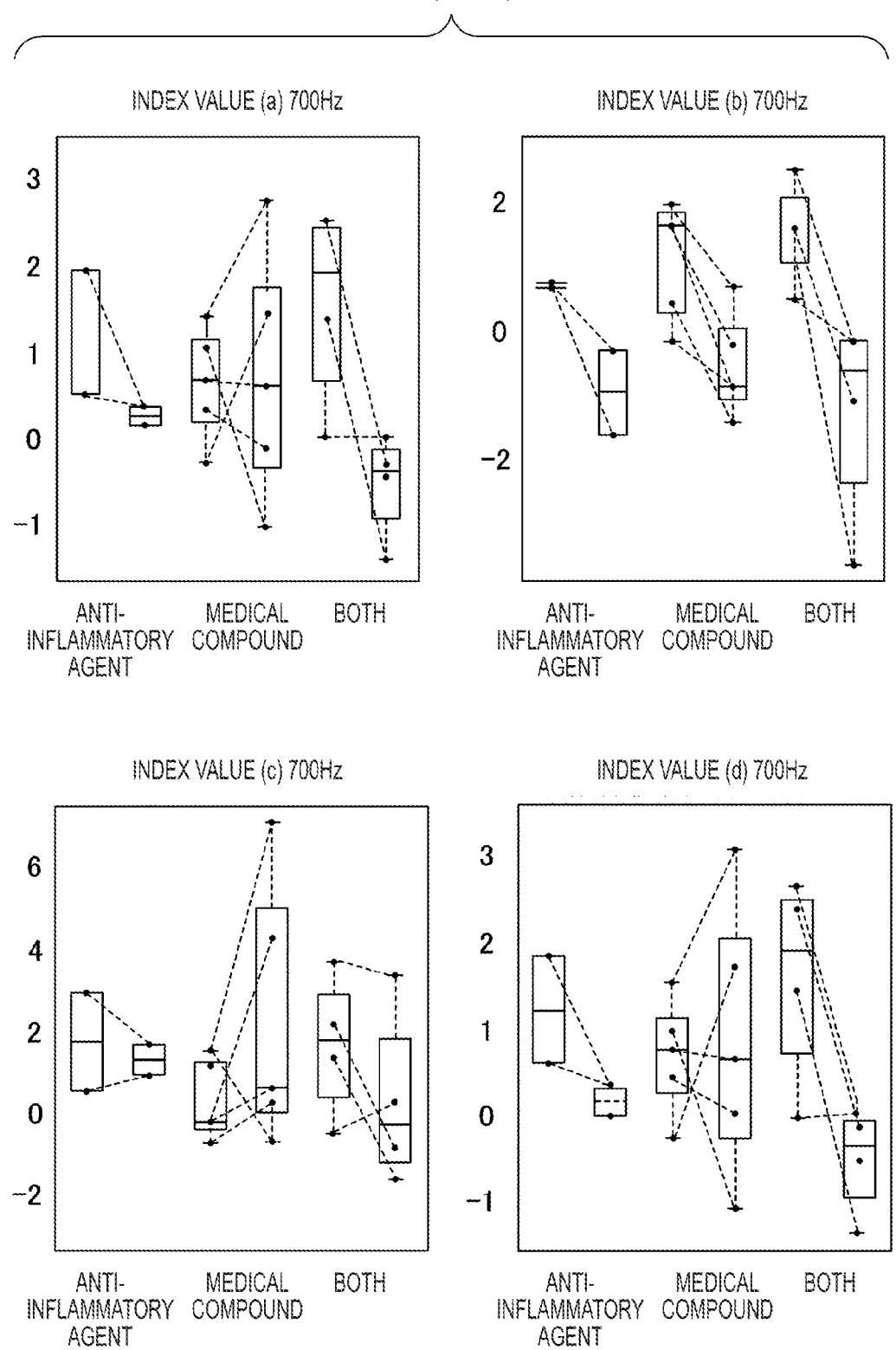
FIG. 10 is a view illustrating examples indicating changes in index value depending on the type of medicine in the bioacoustic sound testing device shown in FIG. 1.

FIG. 10 is a view illustrating examples indicating changes in index value depending on the type of medicine ((1) anti-inflammatory agent, (2) medical compound of anti-inflammatory agent and bronchodilator, and (3) both anti-inflammatory agent and the medical compound). In the figure, the index value (a) is an index value in which the influence of respiratory airflow is reduced, the index value (b) is an index value in which the influence of respiratory airflow and the influence of respiratory tract stenosis are reduced, the index value (c) is an index value in which the influence of respiratory airflow is reduced and the influence of respiratory tract stenosis is emphasized, and the index value (d) is the average value of the index value (b) and the index value (c). The figure shows the distributions of the index values at the start time of the medication and after one month from the start of the medication for each type of medicine, and individual medical cases are connected using dotted lines. In the index value (a), the directions of changes of the index value before and after the medication are divergent, but in the index value (b), a constant trend is found in the change in each medical case regardless of the type of medicine. Since the index value (d) is similar to the index value (a), it can be interpreted that the index value (b) and the index value (c) have been acquired by classifying the index value (a) from different viewpoints. In other words, it is assumed that the change due to the improvement of inflammation have been extracted in the index value (b) by eliminating the influence of respiratory tract stenosis.

As the daily control state of the respiratory tract, it is desired to know whether the control of inflammation is successful, instead of knowing whether the respiratory tract has been dilated using bronchodilator. Bronchodilator literally has the action of dilating the respiratory tract and changes the physical characteristics of the respiratory tract serving as an acoustic tube, whereby the respiratory sound is also changed. However, the control state of the inflammation and the control state of the stenosis are mixed in the state of the respiratory tract appearing in the respiratory sound. In this respect, since the influence of respiratory tract stenosis can be eliminated in the present disclosure, it is possible to know whether the control of the inflammation is successful.

Figure 11:
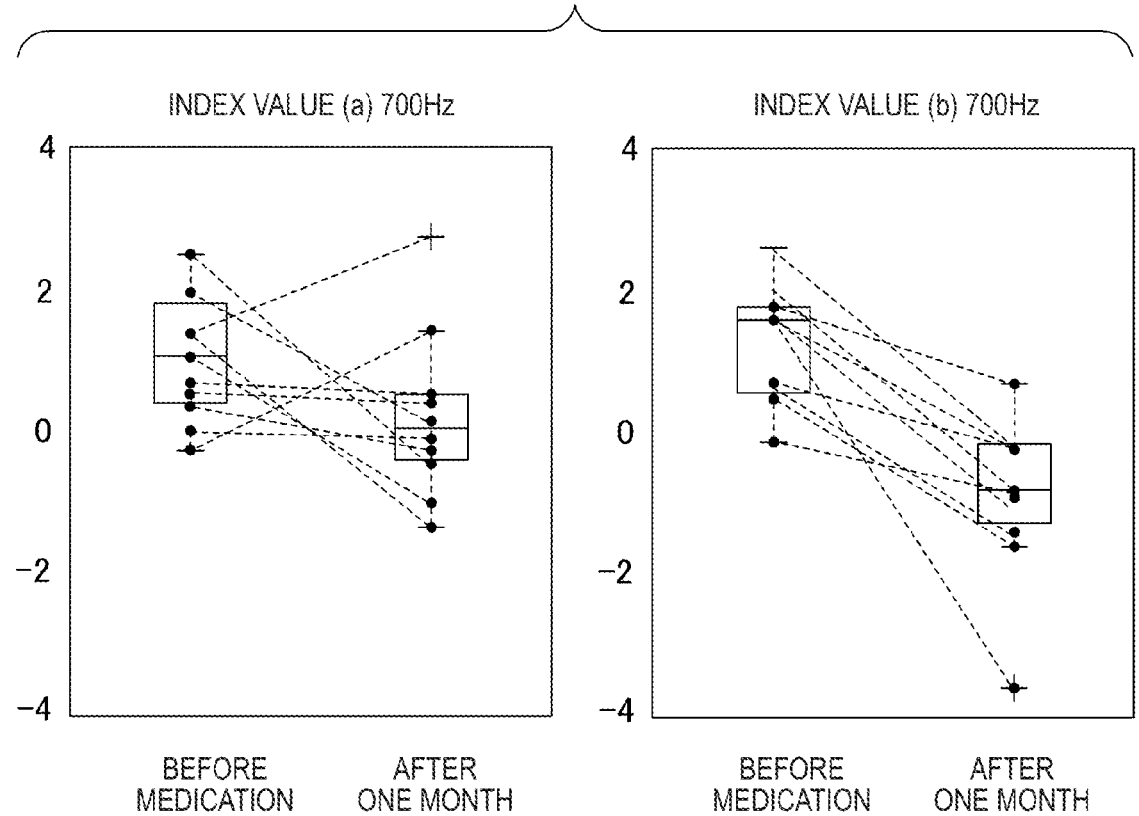
FIG. 11 is a view illustrating the difference between index value (a) and index value (b) in the bioacoustic sound testing device shown in FIG. 1.

FIG. 11 is a view illustrating the difference between the index value (a) and the index value (b). As shown in the figure, the effect size d in the index value (a) was "0.86" and the effect size d in the index value (b) was "2.11". In this way, the effect size relating to the difference between the average values of the index values before and after the medication was greatly improved from "0.86" to "2.11".

Figure 12:
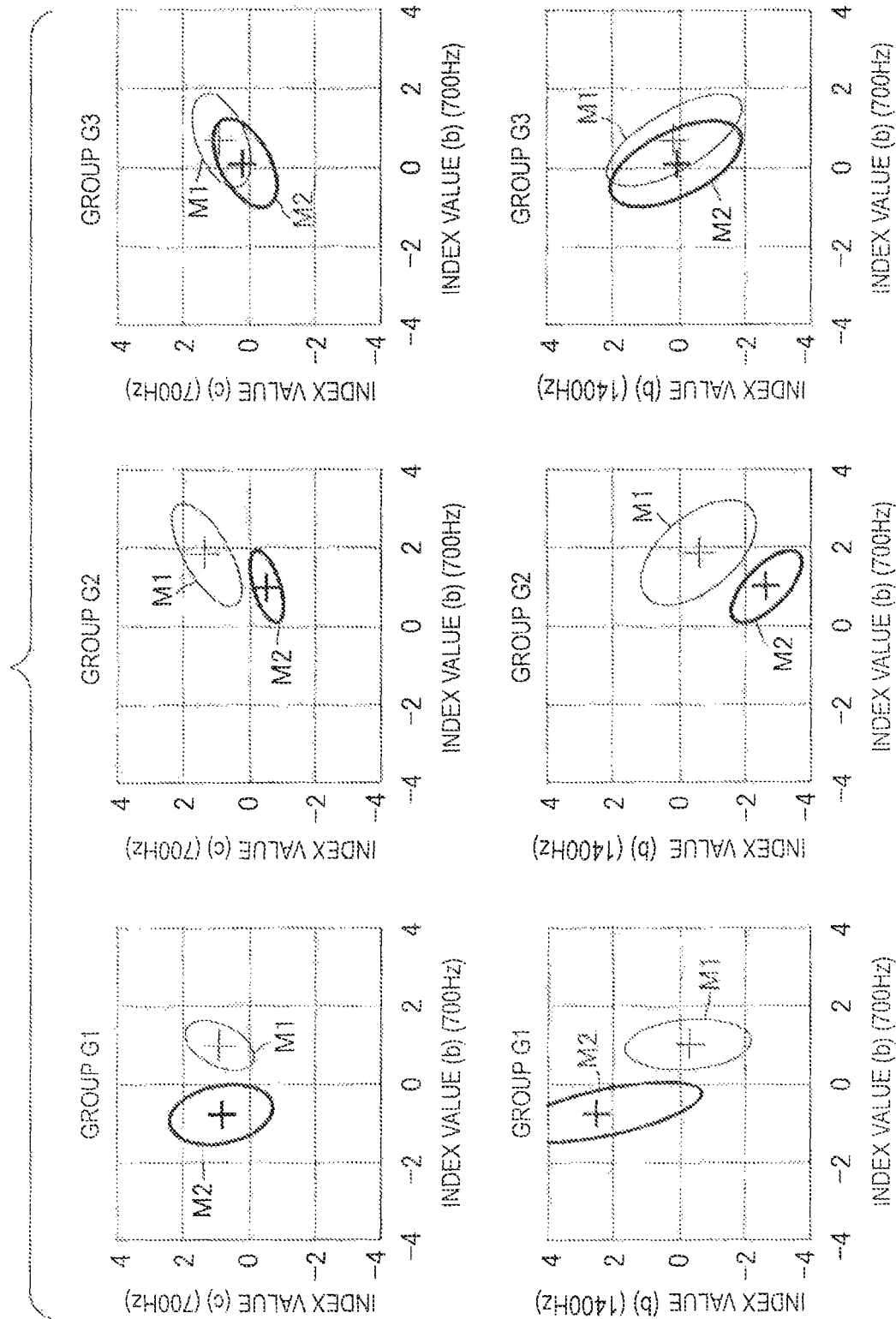
FIG. 12 is a view illustrating examples of analysis maps generated using a plurality of index values.

FIG. 12 is a view illustrating examples of analysis maps generated using a plurality of index values. In the figure, the respective views on the upper stage are two-dimensional maps in which the index value (b) at 700 Hz and the index value (c) at 700 Hz are used, and the respective views on the lower stage are two-dimensional maps in which the index value (b) at 700 Hz and the index value (c) at 1400 Hz are used. In the views on the lower stage, the group G1 is a group medicated with long-term controller, and the distribution of the index values before the medication (indicated in thin line M1) is different from the distribution of the index values after one month (indicated in thick line M2). The index values are moved to the left due to the improvement of the state. Group G2 is a group medicated with 132 stimulant, and the distribution of the index values before the medication (indicated in thin line M1) is different from the distribution of the index values after 20 minutes (indicated in thick line M2). The index values are moved downward due to the improvement of the state. Group G3 is a group subjected to spirometry, and the distribution of the index values in the case that the value of V50 is less than 80 (indicated in thin line M1) is different from the distribution of the index values in the case that the value of V50 is equal to or higher than 80 (indicated in thick line M2). The index values indicating bad states are distributed in the upper right portion. The views on the upper stage are similar to the views on the lower stage in that the movement of the index values is different in the respective groups although the movement along the vertical axis is different.

Figure 13:
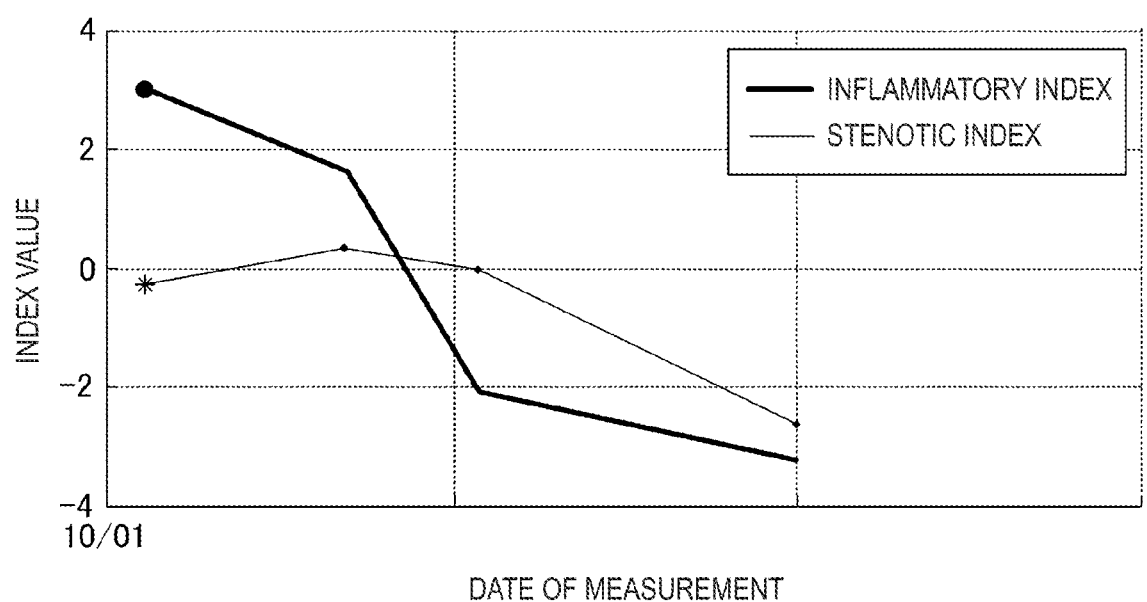
FIG. 13 is a view illustrating an example in which index values are displayed.

FIG. 13 is a view illustrating an example in which the index values are displayed. As shown in the figure, the display 6 of the bioacoustic sound testing device 1 according to this embodiment displays the current index values together with the past index value samples having been stored. It is possible to support the multilateral evaluation of the change in the state of the respiratory tract by tracking two index values for the same person to be measured in time series. In the example shown in the figure, respiratory tract inflammation was improved first and then respiratory tract stenosis was improved.

Figure 14:
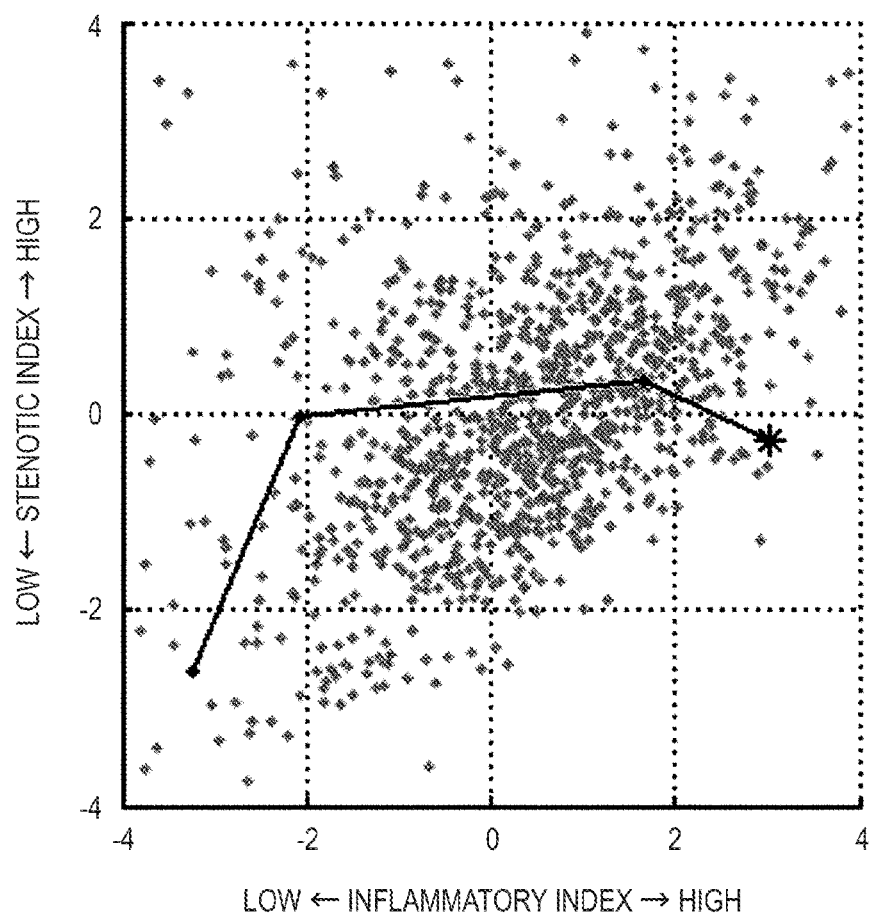
FIG. 14 is a view illustrating another example in which index values are displayed.

FIG. 14 is a view illustrating another example in which the index values are displayed. As shown in the figure, two indexes are separated to the X-axis and the Y-axis, and numerous measurement samples are plotted in the background, and the locus of the change in the index value of a specific person to be measured is plotted, whereby the positions of the index values in the entire distribution can be clarified.

As described above, the bioacoustic sound testing device 1 according to this embodiment calculates the band power in the 15 frequency bands having a bandwidth of 100 Hz and ranging from 100 to 1500 Hz (central frequencies) on the basis of the bioacoustic sound obtained at one point on the chest; calculates the band powers of the eight bands ranging from 300 to 1000 Hz reflecting the respiratory airflow and the band powers of the three bands ranging from 1300 to 1500 Hz reflecting the specific change of the living body, from among the 15 bands ranging from 100 to 1500 Hz; calculates the respiratory airflow reflecting power by averaging the band powers of the bands reflecting the respiratory airflow; calculates the specific change reflecting power by averaging the band powers of the bands reflecting the specific change; obtains the reference power by the linear sum of the calculated respiratory airflow reflecting power and the calculated specific change reflecting power; calculates the difference between the predicted value corresponding to the reference power and the band power for each band as the corrected power; and calculates at least one index value on the basis of the corrected power, whereby an index value properly reflecting the state of the respiratory tract can be obtained while the number of the sensors for measuring the bioacoustic sound is reduced. Furthermore, since the number of the sensors can be reduced, the operation of the apparatus is simplified.

Although linear operations have been described as examples of the operations in this embodiment, the operations may include non-linear operations, such as logarithmic and exponential operations.

Furthermore, the bioacoustic sound testing device 1 according to this embodiment can be achieved using a proprietary circuit configuration or can be achieved using a configuration including a computer. It is also possible to divide processing between the terminal and the cloud.

Moreover, the program shown in FIG. 2 can be stored in storage media, such as a magnetic disk, an optical disk, a magneto-optical disk or a semiconductor memory device and distributed. The program can also be downloaded via a network.

Although the present disclosure has been described in detail referring to the specific embodiments, it is obvious to those skilled in the art that the present disclosure can be changed and modified variously without departing from the spirit and scope of the present disclosure.

The present disclosure has an effect capable of obtaining an index value properly reflecting the state of the respiratory tract while the number of the sensors for measuring bioacoustic sound is reduced, and is applicable to medical apparatuses for supporting the estimation of the state of a living body.

The invention claimed is:

1. A bioacoustic sound testing method of a bioacoustics sound testing system having a single electronic stethoscope, a processor, and a display, the method comprising:
    placing the single electronic stethoscope at one point of a chest of a living body;
    receiving and measuring a bioacoustic sound wave at the one point of the chest of the living body on which the single electronic stethoscope is placed;
    determining, with the processor, a band power in a predetermined period for each of a plurality of predetermined frequency bands on the basis of the bioacoustic sound wave acquired from the single electronic stethescope;
    determining, with the processor, a first power on the basis of a band power of a first band at least partially including any of frequencies ranging from 250 Hz or more to 1050 Hz or less, the first band strongly reflecting a respiratory airflow;
    determining, with the processor, a second power on the basis of a band power of a second band at least partially including any of frequencies ranging from 1250 Hz or more to 1550 Hz or less, wherein the second band is a band in which a power of the bioacoustic sound improved after a medication of bronchodilator to the living body, becomes lower and a power of the bioacoustic sound wave, improved after the medication of anti-inflammatory agent to the living body, becomes higher; and
    determining, with the processor, a reference power by adding the first power to a weighted second power, to reduce an influence of respiratory airflow and an influence of respiratory tract stenosis, and to emphasize a change in a respiratory sound due to an improvement in chronic inflammation;
    determining, with the processor, an index value, to perform analysis as to whether inflammation of a respiratory tract has improved by medication to the living body, on the basis of the reference power and of the band power of a predetermined frequency band, the predetermined frequency band being 700 Hz; and displaying the determined index value on the display, wherein the determining of the index value comprises:

determining, with the processor, a predicted value at the predetermined frequency band on the basis of at least the reference power and prediction coefficients, the prediction coefficients being determined, with the processor, based on the reference power and a standard value of the band power corresponding to the reference power, and the standard value of the band power being predicted based on previously collected bioacoustic sound wave samples at least including samples which are not diagnosed with asthma;

determining, with the processor, a corrected power at the predetermined frequency band by subtracting the predicted value at the predetermined frequency band from the band power at the predetermined frequency band; and setting, with the processor, the corrected power as the index value.

2. The bioacoustic sound testing method according to claim 1, wherein displaying the determined index value on the display comprises displaying the determined index value as values of an inflammatory index along a time axis.

3. A bioacoustic sound testing system comprising:

a single electronic stethoscope that is placed at one point of a chest of a living body and measures a bioacoustic sound wave at the one point of the chest of the living body;

a display;

a memory that stores instructions; and a processor that, when executing the instructions stored in the memory, performs operations including:

receiving, from the single electronic stethoscope, the bioacoustic sound wave at the one point of the chest of the living body;

determining a band power in a predetermined period for each of a plurality of predetermined frequency bands on the basis of the bioacoustic sound wave received by the single electronic stethoscope;

determining a first power on the basis of a band power of a first band at least partially including any of frequencies ranging from 250 Hz or more to 1050 Hz or less, the first band strongly reflecting a respiratory airflow, determining a second power on the basis of a band power of a second band at least partially including any of frequencies ranging from 1250 Hz or more to 1550 Hz or less, wherein the second band is a band in which a power of the bioacoustic sound wave, improved after a medication of bronchodilator to the living body, becomes lower and a power of the bioacoustic sound wave, improved after the medication of anti-inflammatory agent to the living body, becomes higher, determining a reference power by adding the first power to a weighted second power, to reduce an influence of respiratory airflow and an influence of respiratory tract stenosis, and to emphasize a change in a respiratory sound due to an improvement in chronic inflammation; and determining an index value, to perform analysis as to whether inflammation of a respiratory tract has improved by medication to the living body, on the basis of the reference power and of the band power of a predetermined frequency band, the predetermined frequency band being 700 Hz;

wherein the display displays the determined index value, and wherein the determining of the index value comprises:

determining a predicted value at the predetermined frequency band on the basis of at least the reference power and prediction coefficients, the prediction coefficients being determined based on the reference power and a standard value of the band power corresponding to the reference power, and the standard value of the band power being predicted based on previously collected bioacoustic sound wave samples at least including samples which are not diagnosed with asthma;

determining a corrected power at the predetermined frequency band by subtracting the predicted value at the predetermined frequency band from the band power at the predetermined frequency band; and setting the corrected power as the index value.

4. The bioacoustic sound testing system according to claim 3, wherein the display plots the index value along a time axis.

5. The bioacoustic sound testing system according to claim 3, wherein the processor comprises:

a frequency analyzer that performs frequency analysis for a measured bioacoustic sound wave;

a period designator that designates a period to be analyzed from a plurality of respiration periods; and a period representative band power calculator that calculates a representative band power in the period designated by the period designator for the plurality of predetermined frequency bands on the basis of the bioacoustic sound wave subjected to frequency analysis using the frequency analyzer.

6. The bioacoustic sound testing system according to claim 3, wherein the reference power is an average value of the powers of continuous wide bands including the first band and the second band.

7. The bioacoustic sound testing system according to claim 6, wherein the reference power is an average value of the powers of the bands including frequencies ranging from 150 Hz or more to 1550 Hz or less.

8. The bioacoustic sound testing system according to claim 3, wherein the display displays the determined index value as values of an inflammatory index along a time axis.

9. A bioacoustic sound testing system for displaying an index value, the bioacoustics sound testing system comprising:

a display;

a memory that stores instructions; and a processor that, when executing the instructions stored in the memory, performs operations including:

receiving a sound signal which is detected at a sensor, the sensor being placed at one point of a chest of a living body and generating the sound signal by detecting a sound wave at the one point of the chest of the living body;

determining, based on the sound signal, the index value which indicates a degree of inflammation of the living body, displaying, on the display, information indicating the index value, wherein, determining the index value comprises:

determining a first power on the basis of a band power of a first band at least partially including any of frequencies ranging from 250 Hz or more to 1050 Hz or less, determining a second power on the basis of a band power of a second band at least partially including any of frequencies ranging from 1250 Hz or more to 1550 Hz or less, determining a reference power by adding the first power to a weighted second power, determining a corrected power of a predetermined frequency band by correcting band power of the predetermined frequency band based on the reference power, the predetermined frequency band including 700 Hz, determining the index value on the basis of the corrected power.

10. The bioacoustic sound testing system according to claim 9, wherein the memory further stores past index value samples which have been measured with respect to the living body, wherein, displaying information indicating the index value comprises plotting the currently determined index value and the past index value samples, on the display, along a time axis.

11. The bioacoustic sound testing system according to claim 9, wherein the predetermined frequency band further includes both of the first band and the second band.

12. A bioacoustic sound testing method for obtaining an index value indicating a degree of inflammation of a living body, the method comprising:

receiving a sound signal which is detected at a sensor, the sensor being placed at one point of a chest of the living body and generating the sound signal by detecting a sound wave at the one point of the chest of the living body;

determining the index value based on the sound signal, wherein, determining the index value comprises determining a first power on the basis of a band power of a first band at least partially including any of frequencies ranging from 250 Hz or more to 1050 Hz or less, determining a second power on the basis of a band power of a second band at least partially including any of frequencies ranging from 1250 Hz or more to 1550 Hz or less, determining a reference power by adding the first power to a weighted second power, determining a corrected power of a predetermined frequency band by correcting band power of the predetermined frequency band based on the reference power, the predetermined frequency band including 700 Hz, determining the index value on the basis of the corrected power.

13. The bioacoustic sound testing method according to claim 12, further comprising:

acquiring past index value samples which have been measured as to the living body, plotting, on a display, the currently determined index value and the past index value samples, along a time axis.

14. The bioacoustic sound testing method according to claim 12, wherein the predetermined frequency band further includes both of the first band and the second band.

* * * * *